United States Patent [19]

McSpadden

[11] 4,353,698
[45] Oct. 12, 1982

[54] DENTAL TOOL

[75] Inventor: John T. McSpadden, Johnson City, Tenn.

[73] Assignee: Inventive Technology International, Inc., Johnson City, Tenn.

[21] Appl. No.: 297,007

[22] Filed: Aug. 27, 1981

Related U.S. Application Data

[63] Continuation of Ser. No. 105,761, Dec. 20, 1979, abandoned, which is a continuation-in-part of Ser. No. 970,464, Dec. 18, 1978, abandoned.

[51] Int. Cl.³ .............................................. A61C 3/08
[52] U.S. Cl. ..................................... 433/164; 433/32; 433/81; 433/122
[58] Field of Search .................. 433/81, 102, 123, 124, 433/122, 164, 133, 226, 118

[56] References Cited

U.S. PATENT DOCUMENTS

| | | | |
|---|---|---|---|
| 336,777 | 2/1886 | Williams | 433/165 |
| 1,151,352 | 8/1915 | Frink | 433/89 |
| 1,307,446 | 6/1919 | Kerr | 433/102 |
| 1,694,857 | 12/1928 | Kulik | 433/81 |
| 1,753,352 | 4/1930 | Stark | 433/133 |
| 1,771,182 | 7/1930 | Lentulo | 433/164 |
| 3,727,313 | 4/1973 | Graham | 433/133 |

FOREIGN PATENT DOCUMENTS

| | | | |
|---|---|---|---|
| 279144 | 10/1913 | Fed. Rep. of Germany | 433/102 |
| 365050 | 1/1921 | Fed. Rep. of Germany | 433/102 |
| 464121 | 6/1926 | Fed. Rep. of Germany | 433/102 |
| 484480 | 10/1928 | Fed. Rep. of Germany | 433/81 |
| 519086 | 2/1931 | Fed. Rep. of Germany | 433/164 |
| 775073 | 12/1934 | France | 433/102 |

*Primary Examiner*—Gene Mancene
*Assistant Examiner*—John J. Wilson
*Attorney, Agent, or Firm*—Luedeka, Fitch & Neely

[57] ABSTRACT

Disclosed is a dental tool for obturating stripped root canals, comprising an elongated rod-like body having a shank or handle and a working portion with radially outwardly extending shoulders or flutes facing away from the shank and making an angle with the longitudinal axis of the body of about 90° or less. The diameter of the shoulders or flutes may be progressively diminished from adjacent the shank toward the end of the working portion to provide a taper, and in another embodiment the shoulders are continuous and spiraled. In use, the tool may be linearly and angularly reciprocally mounted in a power operator, and may be heated for softening the obturating materials, such a gutta-percha. The reciprocation of the tool, particularly the linear reciprocation, forces the shoulders into compressive contact with the softened material and, when adequate density is attained, backs out of the root canal naturally through reverse action without specific operator effort. Preferably, the flutes are doubled and continuous and means is provided to rotate the tool at high rpm, oppositely to the direction of the spiral.

1 Claim, 4 Drawing Figures

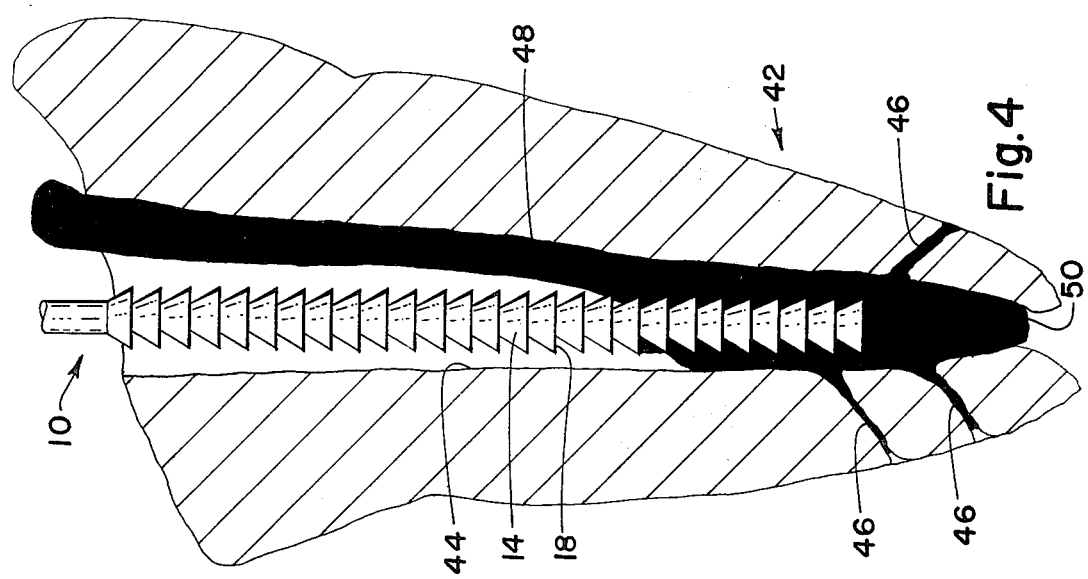
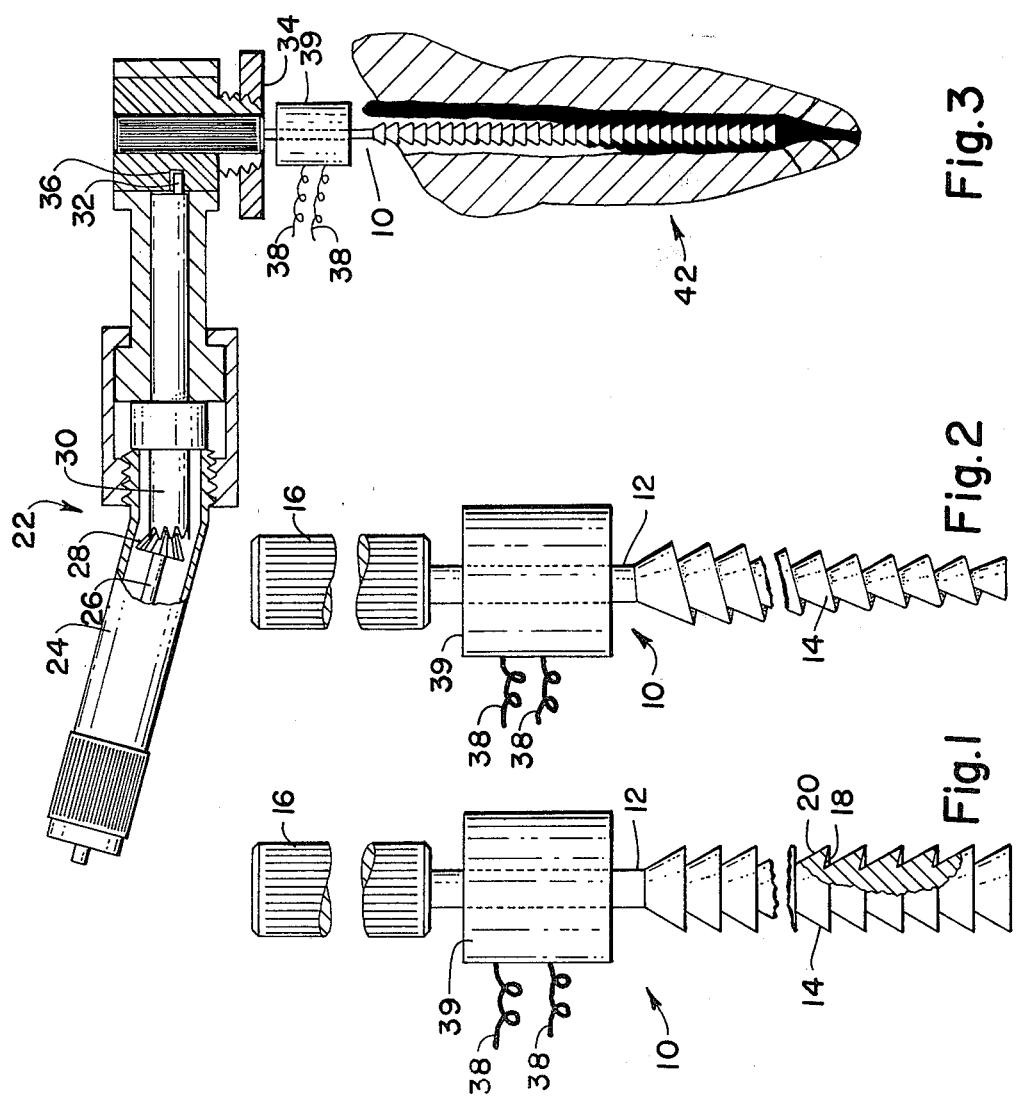

DENTAL TOOL

This is a continuation of application Ser. No. 105,761, filed Dec. 20, 1979, now abandoned, and which is a continuation in part of Ser. No. 970,464, filed Dec. 18, 1978 now abandoned.

This invention relates to the field of dentistry and in particular to novel means for inserting and compacting filler material into the extirpated root canals of teeth.

In the field of dentistry, one of the most technically difficult mechanical operations is that of obturating (filling) a stripped (extirpated) root canal. The difficulty arises from the necessity to totally fill the root canal void in a homogeneous three-dimensional manner in order to prevent any leakage or communication between the root canal system and the surrounding and supporting tissues of the tooth.

The filler material is conventionally thermoplastic, strandlike pieces of gutta-percha known as points, which typically is inserted into the stripped root canal and then physically compacted (condensed) by small compacting tools known as pluggers and spreaders. These tools are heated to soften the gutta-percha points in the canal and then hand manipulated to progressively feed and compact the points in the canal. Additional points are fed to the canal as the compacting proceeds in order to completely fill the void. An extensive disclosure of the various root canal tools may be found in Chapter 12, and its cited references, of the textbook, *Pathways of the Pulp*, University of the Pacific School of Dentistry, published by The C. V. Mosby Company, St. Louis, 1976, and edited by Stephen Cohen and Richard C. Burns.

As aforesaid, one of the major difficulties involved in this procedure is that the canal must be completely filled three-dimensionally, obliterating any accessory canals and plugging as many openings to the external surface of the tooth as possible. In order to accomplish this feat, the dentist must employ consummate skill and a great deal of time.

The present invention has as its objects, to reduce the technical difficulties and also the time involved in obturating stripped root canals, and to provide convenient, substantially automatic, and easily manipulatable means for performing the obturation.

These and further objects hereinafter appearing have been attained in accordance with the present invention through the discovery of a unique and unobvious compacting tool which is easily operable with much more efficiency and speed, either by hand or by power operator, than known compacting tools.

The invention is defined in its broad sense as a compactor comprising a handpiece-bit combination, said bit having a shank portion and a working portion, flute means on said working portion facing away from said shank portion and making an angle with the longitudinal axis of said body of about 90° or less, said handpiece gripping the shank portion of said bit and adapted to rotate said bit at between about 3,500 and 20,000 rpm. The shoulder or flute means may be continuous and spiraled, single or double, preferably double, and the diameter thereof may be progressively diminished along the working portion to provide a taper. The double flutes are obtained by starting two flute cuts 180° apart in known manner, and the resulting tool has been found to be much more resistant to breakage than the single flute embodiment.

The invention will be further understood from the following description and drawing wherein:

FIG. 1 is a partial cross-sectional view of an embodiment of the obturating tool;

FIG. 2 is a partial cross-sectional view of the spiraled embodiment of the tool;

FIG. 3 is a partial cross-sectional view of the tool with heater and power actuator attached; and FIG. 4 is a cross-sectional view of a tooth with the tool in working position.

Referring to the drawings, the obturating tool generally designated 10 and being about 1-2 inches long, comprises a body having a shank portion 12 and a working portion 14, each of which may have various cross-sectional configurations including rectangular, triangular, and preferably round. An enlarged end 16 on the body, which may be an enlarged portion of the shank, may be provided for manual or chuck gripping as hereinafter described. A plurality of shoulders or flutes 18 are provided on the working portion and may circumscribe the body in a continuous, uniform manner as shown in FIG. 1, or may be irregular, e.g., discontinuous and/or undulating. These shoulders or flutes (360° section of the continuous flute) preferably number between about 0.1 to about 5.0 per millimeter, and most preferably between about 0.5 and about 2.0 per millimeter. The shoulders are cut or otherwise formed such that they make approximately a right angle or less with the longitudinal axis of the tool body. Severe undercuts, such as 45° or so, are unnecessary and not preferred. An angle of from about 70° to 90° is entirely adequate to achieve good feeding and compaction of the filler material without undue adherence of the gutta-percha to the shoulders 18. The angle preferably is from about 90° to about 80°. The shoulder diameters may be progressively reduced as shown in FIG. 2 to provide a tapered tool, or may be straight as shown in FIG. 1. In the embodiment of FIG. 2, the shoulder means is also continuous and spiraled. When so spiraled, the aforesaid number of shoulders per millimeter refers to the number of complete spirals per flute, per millimeter. As aforesaid, the flutes of this spiraled embodiment are preferably double. The outer diameter of the shoulders may vary between for example, about 2.5 mm. and about 0.2 mm. as required by the various stages of the obturation procedure and also for different size root canals. The inside diameter of the shoulders should be sufficient to provide adequate strength to the tool body, while allowing adequate surface area for the shoulders to function properly. The diameters may be reduced by a proportional amount for the tapered tools. Surfaces 20 are preferably straight and immediately tapers from the outside diameter of the shoulder of the flute toward the inside diameter of the adjacent shoulder, as clearly shown in FIGS. 1-4, so that there is a minimal peripheral land or flat surface at the outside diameter of the flute. It is also contemplated that the surface 20 be concave or convex. Preferred materials for the tool are stainless and carbon steel. The enlarged end or handle 16 is typically molded plastic but may be of any structural material including metal and may be integral with the shank and of any size. Usually, small plastic handles are molded onto the root canal tools such as compactors, condensers, files, pluggers, reamers, and the like, and such may be done with the present tool.

As shown in FIG. 3, the tool may be power actuated by mounting in a hand-held actuator such as 22. Such actuators generally comprise a housing 24 is which is mounted a drive shaft 26, drive gear 28, power take-off shaft and gear assembly 30, actuator cam 32, and reciprocative chuck or tool holder 34 provided with a cam follower recess 36 which is oversized to allow for the angular, reciprocating rotation. Generally a linear reciprocation travel for the chuck of about 2.0 millimeters, and an angular reciprocation of about 20°, is quite functional. The angular reciprocation assists in proper release of the filler material from the shoulders 18. Such construction is typical for these power actuators. Shaft 26 may be connected, for example, by a suitable chuck to the output shaft of an air driven or electric motor which may be powered from a wall outlet or batteries, and provided with any necessary gear reduction to give the proper reciprocation frequency for the obturating tool. The preferable power actuator for the double fluted tool is a high speed, 3,500–20,000 rpm, preferably about 8,000–15,000 rpm, air driven actuator which is a non-reciprocating type and rotates the tool oppositely to the direction of the spiral, e.g., counterclockwise in FIG. 2. It is noted that the flutes may be in the opposite direction to that of FIG. 2, in which case the power actuator would rotate the tool in a clockwise direction. The type of power actuator for the tool also is not limiting of the invention in any way, and the aforementioned textbook may be referred to also for a description of some of the available reciprocating power actuators.

Any convenient electric heater such as a wall plug-in, A.C. resistance heater coil, may be employed to heat the tool for softening the gutta-percha. The heater may heat by convection, conduction, or radiant, and its construction may be widely varied. As examples, an electric induction heater may be mounted in the actuator housing portion in which chuck 34 reciprocates, or an electrical nichrome resistance heater wire 38 may be coiled around the tool shank or chuck, imbedded in ceramic collar 39 and connected to a power source such as the aforesaid wall outlet or the aforesaid rechargeable batteries. The lead portions of wire 38, obviously may be housed or sheathed by known means to satisfy the necessary safety and appearance requirements. A thermostat, manually or automatically operable, may be connected into the heater circuit to regulate the temperature of tool 10 such that proper softening of the gutta-percha can be maintained by the dentist.

In a preferred embodiment of the heating element and control circuit for the tool, the element consists of resistance wire of nichrome of 12–16 mil diameter in thermal contact with the tool body. The control circuit consists of variable resistance and/or variable pulse length controller (SCR or similar). The control permits the temperature of the tool to be varied by varying the current and voltage amplitude of the electrical signal. An optional temperature sensor, e.g., thermocouple or temperature-sensitive resistance, can be utilized to provide thermostatic and automatic control of the temperature in addition to operator control. The power supply to the control circuit is 110 V transformed to below about 12 V.

Referring to FIG. 4, a tooth 42 is shown in cross section with the root canal 44 extirpated. A few auxiliary canals 46 are shown. A gutta-percha tip 48 has been inserted into the canal and is in the process of being softened and compacted by bit 14 which is being linearly and angularly reciprocated by a power actuator. As heat is applied to the gutta-percha by the heated tool, the reciprocating shoulders 18 feed and force it down in the canal toward the apex 50, and when the density thereof is sufficiently high, the bit backs out of the canal autmoatically through natural reverse action. In the continuous, double fluted embodiment, the high speed rotation of the tool generates sufficient heat to maintain the gutta-percha at the proper fluidity for the filling operation, and an additional heat source is not required. By means of this device and technique, much greater uniformity of density and completeness of fill is experienced in a small fraction of the time which manual obturation would require.

Although the invention has been described in considerable detail with particular reference to certain preferred embodiments thereof, variations and modifications can be effected within the spirit and scope of the invention.

I claim:

1. A compactor for gutta-percha comprising a bit having a shank portion and a working portion, flute means on said working portion defining a continuous spiral flute having a shoulder facing away from said shank portion and making an angle with the longitudinal axis of said working portion of from about 90° to about 80°, the diameter of said flute means progressively decreasing away from said shank portion to provide a tapered working portion, said continuous spiraled flute making from about 0.5 to about 2.0 spirals per millimeter along the longitudinal axis of said working portion, and said continuous spiral flute having a surface which immediately tapers from the outside diameter of said shoulder of said flute toward the inside diameter of an adjacent shoulder so that there is a minimal peripheral land at the opposite diameter of said continuous spiral flute.

* * * * *

UNITED STATES PATENT AND TRADEMARK OFFICE
CERTIFICATE OF CORRECTION

PATENT NO. : 4,353,698
DATED : October 12, 1982
INVENTOR(S) : John T. McSpadden

It is certified that error appears in the above—identified patent and that said Letters Patent is hereby corrected as shown below:

Column 4, line 49, "opposite" should be -- outside --.

Signed and Sealed this

Sixteenth Day of August 1983

[SEAL]

Attest:

GERALD J. MOSSINGHOFF

Attesting Officer     Commissioner of Patents and Trademarks